United States Patent [19]
Vogel et al.

[11] Patent Number: 5,756,724
[45] Date of Patent: May 26, 1998

[54] HIGH-YIELDING ULLMANN REACTION FOR THE PREPARATION OF BIPYRROLES

[75] Inventors: Emanuel Vogel, Köln; Reiner Deponte, Cologne, both of Germany

[73] Assignee: Cytopharm, Inc., Menlo Park, Calif.

[21] Appl. No.: 844,904

[22] Filed: Apr. 22, 1997

[51] Int. Cl.⁶ ............... C07D 403/04; C07D 487/22
[52] U.S. Cl. ............................. 540/145; 548/518
[58] Field of Search ..................... 540/145; 548/518

[56] References Cited

U.S. PATENT DOCUMENTS

| | | | |
|---|---|---|---|
| 4,913,907 | 4/1990 | Jori et al. | 424/450 |
| 5,015,478 | 5/1991 | Jori et al. | 424/450 |
| 5,132,101 | 7/1992 | Vogel et al. | 424/9 |
| 5,179,120 | 1/1993 | Vogel et al. | 514/410 |
| 5,244,671 | 9/1993 | Vogel et al. | 424/450 |
| 5,262,401 | 11/1993 | Vogel et al. | 514/410 |

*Primary Examiner*—Joseph McKane
*Attorney, Agent, or Firm*—Oblon, Spivak, McClelland, Maier & Neustadt, P.C.

[57] ABSTRACT

Coupling two moles of a 2-halopyrrole in the presence of an inert aromatic solvent and a catalytically effective amount of a substantially pure copper catalyst provides high yields of the corresponding bipyrrole.

16 Claims, No Drawings

HIGH-YIELDING ULLMANN REACTION FOR THE PREPARATION OF BIPYRROLES

DISCUSSION OF THE BACKGROUND

1. Field of the Invention

The invention relates to a novel high-yielding Ullmann reaction for the preparation of bipyrroles. Bipyrroles are used in the preparation of porphycene compounds which have been demonstrated to have utility in photodynamic therapy.

2. Discussion of the Background

Porphycenes are isomers of porphyrins. Porphycenes have been shown to be highly effective photoactivatable dyes of utility in photodynamic therapy. See U.S. Pat. No. 4,913,907; U.S. Pat. No. 5,015,478; U.S. Pat. No. 5,132,101; U.S. Pat. No. 5,179,120; U.S. Pat. No. 5,244,671; U.S. Pat. No. 5,262,401; and U.S. Pat. No. 5,409,400.

The Ullmann reaction is a well known reaction for synthesis of biaryl compounds, typically coupling two phenyl halides to produce biphenyl compounds. It is also possible to couple halonaphthalenes. Several different catalysts have been used for the Ullmann reaction, including commercially available mechanically pulverized copper-bronze, either without pretreatment or after "activation" by washing with acetone solutions of iodine and then hydrochloric acid. Lithographic bronze containing fatty acids, partly as copper salts, and the use of electrolytic copper milled with stearic acid have been used as a catalyst for the Ullmann reaction. See U.S. Pat. No. 2,907,799 and Fanta, P.E., Chemical Reviews (1964), 64: 613–632 and the references cited therein.

One of the key steps in the multi-step synthesis of appropriately substituted bipyrroles, used as intermediates in the synthesis of the tetrapyrrole porphycene ring system, is an Ullmann reaction in which 2-halopyrroles are coupled with elimination of the halogen in the presence of a copper-bronze catalyst.

Conventional Ullmann reaction catalysts and solvents have been largely used in laboratory scale reactions. However, these conventional reaction conditions result in relatively low product yields. Further, the Ullmann reaction is an exothermic reaction which presents difficulties with scale up of Ullmann reactions to industrial scale reactions. When the Ullmann reaction is used to prepare bipyrroles using the conventional copper-bronze catalyst, yields are generally in the range of only about 60–70%. A need continues to exist for improved methods of preparing bipyrroles in order to increase the yield of the Ullmann reaction, increased recovery of waste solvent, reduce the danger of large scale Ullmann reactions, and thereby increase the overall yield of a multistep synthesis of porphycenes utilizing the Ullmann reaction.

SUMMARY OF THE INVENTION

Accordingly, one object of this invention is to provide an improved process for preparing bipyrroles by coupling appropriately substituted halopyrroles using an improved catalyst/solvent combination. The process of the invention provides improved product yields and better control of the exothermic reaction for industrial scale processes. The reaction of the invention also enables one to recover waste solvent and avoid generating waste water thereby providing a process which is more environmentally acceptable.

A further object is to provide a high-yielding Ullmann reaction for use in porphycene synthesis.

These and other objects which will become apparent in the course of the following description of exemplary embodiments have been achieved by the present invention in which two halopyrroles are coupled using copper powder as a catalyst and a high boiling aromatic solvent system.

DETAILED DESCRIPTION OF THE PREFERRED EMBODIMENTS

The method of the present invention provides a method of producing a bipyrrole in high yield of 90% or greater, preferably 95% or greater, even more preferably 98% or greater, in contrast to prior art processes which provide a yield of only about 60–70%.

In the method of the invention, two molecules of a 2-halopyrrole are coupled in the presence of a copper catalyst to form a bipyrrole according to the reaction scheme shown below using a high boiling aromatic solvent.

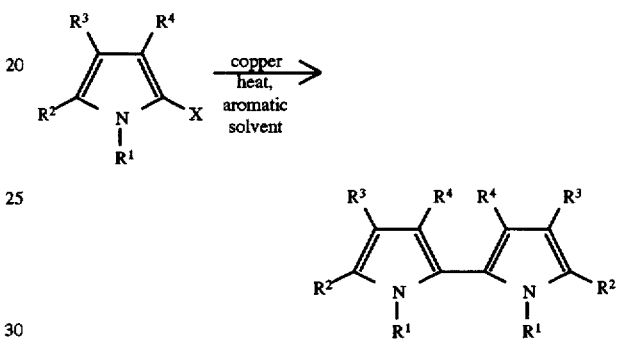

In this reaction scheme, X is a halogen (Cl, Br, I), preferably iodine.

$R^1$ is hydrogen or a group of the formula $C(O)—OR^5$ where $R^5$ is an alkyl, arylalkyl or aryl group. Suitable alkyl groups contain 1–10 carbon atoms, preferably 4–10 carbon atoms; suitable aryl groups contain 6–10 carbon atoms, preferably phenyl; and suitable arylalkyl groups include 1–10 carbon atoms in the alkyl moiety and 6–10 carbon atoms in the aryl moiety. The alkyl group may be straight-chain or branched. $R^1$ is more preferably t-butoxycarbonyl (BOC).

$R^2$ is a group of the formula $C(O)—OR^5$, where $R^5$ is as described above. $R^2$ is preferably ethoxycarbonyl.

$R^3$ is hydrogen, alkyl, alkoxyalkyl or a group of the formula $C(O)—OR^5$. Suitable alkyl groups are straight-chain or branched and contain 1–10 carbon atoms, preferably 1–6 carbon atoms and include methyl, ethyl, propyl, butyl, pentyl, and hexyl groups. Suitable alkoxyalkyl groups include $C_{1-10}$ alkyl groups substituted with a $C_{1-6}$ alkoxy group, preferably $C_{1-6}$ alkyl groups substituted with one $C_{1-6}$ alkoxy group including $C_{1-6}$ alkoxymethyl, $C_{1-6}$ alkoxyethyl, $C_{1-6}$ alkoxypropyl, $C_{1-6}$ alkoxybutyl, $C_{1-6}$ alkoxypentyl, and $C_{1-6}$ alkoxyhexyl groups. Groups having the formula $C(O)—OR^5$ may be the same groups as described above for $R^1$ and $R^2$.

$R^4$ is any of the groups described above for $R^3$. Further, $R^3$ and $R^4$ may be identical or different. When $R^3$ or $R^4$ is $C(O)OR^5$, it is preferable that $R^1$ is hydrogen in order to obtain the highest possible yield. When $R^3$ and $R^4$ are hydrogen, alkyl or alkoxyalkyl, it is preferable that $R^1$ is $C(O)OR^5$ to obtain the best yields in the coupling reaction.

When $R^3$ is alkoxyalkyl and $R^4$ is hydrogen, it is preferred that $R^1$ is hydrogen.

The starting 2-halopyrrole compounds are commercially available or may be readily synthesized using methods well known to those having ordinary skill in synthetic organic chemistry. For example, suitably substituted 2-halopyrrole compounds may be prepared as described in U.S. Pat. No. 5,179,120.

The copper catalyst is substantially pure copper. That is, the catalyst used in the method of this invention differs from prior art processes which utilize copper-bronze or copper containing fatty acids, fatty acid salts, etc. The copper may be present in any suitable physical form including rings, pellets, powder, strips, etc. A particularly preferred form is powdered copper. As used herein, the term "substantially pure copper" means copper which does not contain bronze or other catalyst adjuvants, poisons, modifiers, etc., although the copper catalyst may contain minor amounts of impurities which do not affect the performance of the catalyst. Suitable copper is commercially available from the Aldrich Chemical Co. Inc., (No. 20,778-0), Merck (No. 2703.0250), Norddeutsche Affinerie (FL), etc. at a purity of at least 99.0 wt. %, preferably 99.0–999.99 wt. % pure in the form of a foil, powder, rod, shot, turnings, and wire. The use of copper powder reduces the cost of the reaction since it is not necessary to utilize more expensive modified copper catalysts. This cost savings is important for industrial scale reactions. Further, copper powder is preferred since copper powder is easier to handle, for example, is more easily filtered, than conventional copper-bronze catalysts.

The reaction is conducted by heating two moles of the halopyrrole in the presence of the copper catalyst at a reaction effective temperature. The reaction is preferably conducted with an inert solvent. Suitable inert solvents are aromatic hydrocarbon solvents, for example, aromatic hydrocarbons containing 6–20 carbon atoms. The aromatic solvent compounds may have fused rings and may contain alkyl or aryl substituents. Examples of suitable solvents include benzene, toluene, o-xylene, m-xylene, p-xylene, cumene, o-cymene, m-cymene, p-cymene, naphthalene, etc. and mixtures thereof. Haloalkane solvents are generally unsuitable. Dimethylformamide (DMF) may be used, but tends to generate both lower yields and waste water. The reaction may be conducted at any effective reaction temperature, generally in a temperature range of about 75°–250° C., preferably about 100°–200° C. Conveniently, the reaction is conducted by heating the halopyrrole and solvent under reflux conditions at atmosphere pressure. However, the reaction may be conducted under reduced or super-atmospheric pressure if desired.

The bipyrrole product may be isolated using conventional methods such as extraction, recrystallization, or purification using a separation column. Such methods are well known in the art and can be easily applied to purify the reaction product.

After coupling to produce a bipyrrole, the nitrogen-protecting group may be removed by thermal decarboxylation (200° C., 15 Torr). The ester group (—$CO_2R^5$) can be replaced with hydrogen by alkaline hydrolysis, e.g., alkaline hydrolysis using conventional chemical reactions. Any suitable alkaline hydrolysis method may be used. KOH/MeOH/$H_2O$ followed by thermal decarboxylation gives products in which the ester protecting group has been replaced with a hydrogen as shown below where $R^3$ and $R^4$ are hydrogen, alkyl or alkoxyalkyl groups and $R^5$ is as defined above.

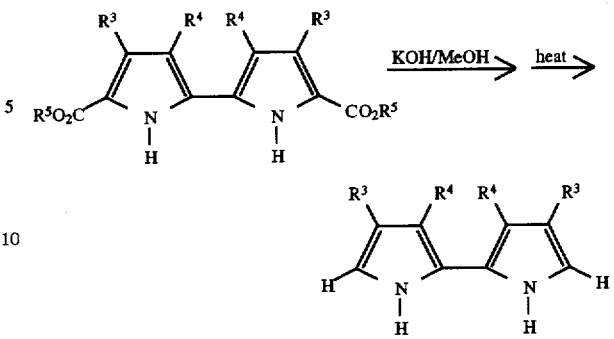

In a preferred process hydrolysis and decarboxylation are carried out in one step by refluxing the educt in an ethylene glycol/NaOH system (as shown, page 11).

The bipyrroles prepared by the process of this invention may be used in a multi-step synthesis to prepare the porphycene compounds for photodynamic therapy. Typically, the bipyrrole is further reacted with $POCl_3$ and dimethylformamide or other suitable reactant to form the corresponding bipyrrole dialdehyde. Two moles of the bipyrrole dialdehyde may then be coupled with a McMurry reaction utilizing low valence titanium (for example, $Ti^{+2}/Ti^{+3}$) in a non-reactive solvent. See, for example, McMurry and Fleming, J. Am. Chem. Soc., (1974), 96: 4708; McMurry, Chem. Rev., 989, 89: 1513; Lenoir, Synthesis, (1989), 883, Mukaiyama et al, Chem. Let., (1973), 1041 and U.S. Pat. No. 5,179,120. A reaction scheme showing the conversion of the bipyrrole product of this invention to the corresponding porphycene is shown below where $R^3$ and $R^4$ are, independently, hydrogen, alkyl or alkoxyalkyl.

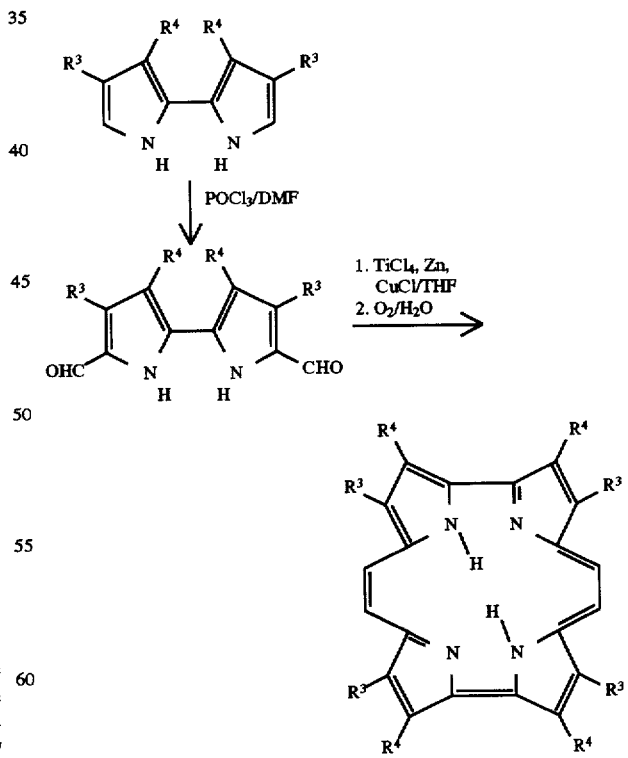

The porphycene compounds so produced are useful in photodynamic therapy as described in U.S. Pat. No. 4,913,907; U.S. Pat. No. 5,015,478; U.S. Pat. No. 5,132,101; U.S.

Pat. No. 5,179,120; U.S. Pat. No. 5,244,671; U.S. Pat. No. 5,262,401 and U.S. Pat. No. 5,409,900. The disclosure of these U.S. patents is incorporated herein by reference for a more complete description of the use of the porphycene compounds in photodynamic therapy.

EXAMPLES

Example 1

Preparation of 5, 5'-diethoxycarbonyl-3,3'-4,4'-tetraethyl-2,2-bipyrrole

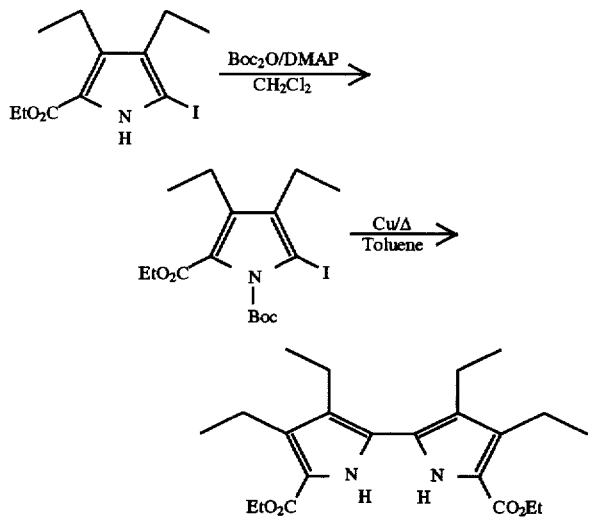

Into a 200 mL Erlenmeyer flask equipped with a magnetic stirrer was placed 2-iodo-5-ethoxycarbonyl-3,4 diethylpyrrole (16.05 g, 50 mmol), BOC-anhydride (12.00 g, 55 mmol), 4-dimethylaminopyrridine (DMAP, 0.15 g) and dichloromethane (75 mL). This mixture was stirred for 1.5-2 hours at room temperature (DC control, silica gel hexane/acetic ester 6:1) to form Boc-protected iodopyrrole.

After completion of the reaction, silica gel (10.00g) was added, the mixture was stirred for about 5 minutes and washed with dichloromethane. The clear, golden-yellow filtrate was completely freed of solvent and then used for the Ullmann reaction without further purification.

Copper powder (20.00 g, not copper-bronze) and toluene (5 mL) were added to the filtrate prepared as described above (about 21. 1 g) and boiled under reflux for about 8–20 hours with DC control (oil bath 135°–140° C., magnetic stirring) until no further reaction was observed.

The reaction mixture was cooled to room temperature and filtered with CELITE. The reaction vessel and the filter were rinsed with toluene and the toluene was added to the reaction mixture. Removal of solvent provided a clear brown filtrate.

The brown filtrate was then heated on an oil bath (about 200°–210° C.) under membrane pump vacuum to completely remove the BOC protective group and to form a pyrolysis residue at which point a stable vacuum pressure was observed.

Hexane (30 mL) was added to the pyrolysis residue after the residue had cooled to room temperature and this mixture was then boiled under reflux using a hot water bath until a major portion of the solid had dissolved (approximately 30 min). This solution was allowed to crystallize overnight in a refrigerator, suctioned off and washed with ice-cold hexane. Yield: about 8.9 g (91.6%).

The bipyrrole diester was subjected to alkaline hydrolysis using ethylene glycol/NaOH to provide the tetraethyl bipyrrole.

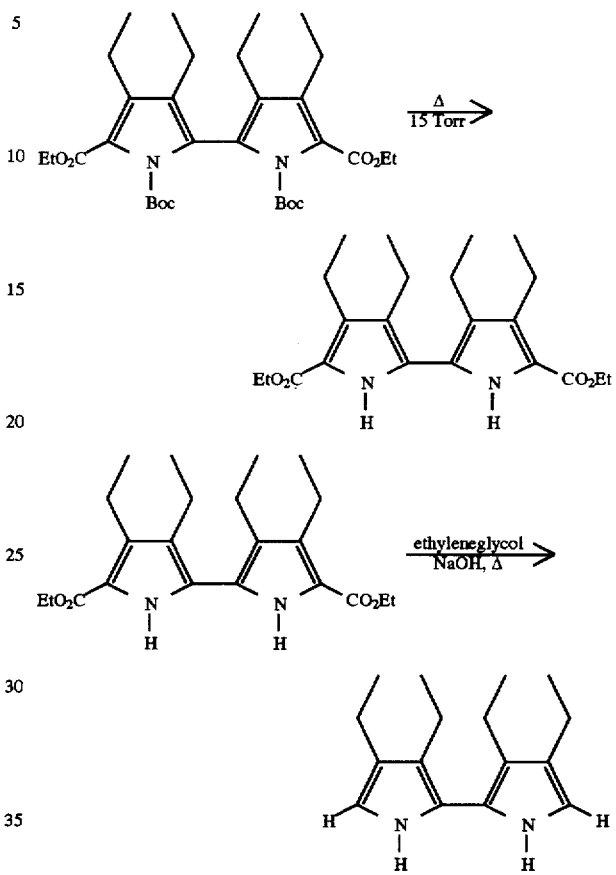

Example 2

Preparation of 2,3,6,7,12,13,16,17-octaethylporphycene

Distilled phosphoryl chloride (POCl$_3$, 40 mmol) is added dropwise to a solution of the tetraethyl bipyrrole (10 mmol) in 50 mL of absolute dimethylformamide (DMF) under protective gas at 0° C. within 30 minutes. The mixture is heated to 60° C. for 1 hour and subsequently poured into a solution of 60 g sodium acetate in 480 mL of water. The mixture is stirred for 1 hour at 85° C., whereupon the corresponding dialdehyde precipitates out. The solution is cooled and the precipitate filtered off and washed with cold water.

Under protective gas over 10 minutes, TiCl$_4$ (0.15 mol) is added dropwise to a suspension of zinc powder (0.3 mol) and CuCl (9.5 mmol) in 800 mL of THF freshly distilled over LiAlH$_4$. Subsequently, the mixture is heated under reflux for 3 hours. The dialdehyde (6 mmol) in 600 mL of absolute THF is added dropwise within 30 minutes to the black McMurry reagent thus prepared while stirring vigorously. The reaction can be followed by means of thin layer chromatography (silica gel/CH$_2$Cl$_2$). The reaction is stirred for 10 minutes at the boiling temperature of the THF and then cooled to 0° C. At this temperature, 300 mL of 6% NH$_3$ solution is added dropwise over 1 hour. The reaction mixture is then treated with 600 mL of dichloromethane and filtered through CELITE after 15 minutes of stirring. The residue is extracted with 200 mL of dichloromethane and the combined organic phases are washed with 300 mL of water. After drying, the solvent is removed under vacuum to provide the porphycene product.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method of preparing a bipyrrole, comprising the step of:

heating a 2-halopyrrole of the formula

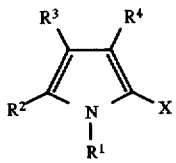

wherein

X is a halogen;

$R^1$ is hydrogen or a group of the formula $C(O)$—$OR^5$ where $R^5$ is an alkyl, arylalkyl or aryl group;

$R^2$ is a group of the formula $C(O)$—$OR^5$ where $R^5$ is as described above;

$R^3$ and $R^4$ are, independently, hydrogen, alkyl, alkoxyalkyl or a group of the formula $C(O)$—$OR^5$ where $R^5$ is as described above;

in the presence of an inert aromatic solvent and a catalytically effective amount of a substantially pure copper catalyst to form a bipyrrole of the formula

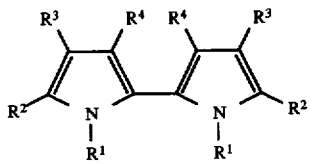

wherein $R^1$, $R^2$, $R^3$, and $R^4$ are as described above.

2. The method of claim 1, wherein X is I.

3. The method of claim 1, wherein $R^1$ is H.

4. The method of claim 1, wherein $R^1$ is C(O)—$OR^5$ and $R^5$ is $C_{1-10}$ alkyl.

5. The method of claim 1, wherein $R^3$ and $R^4$ are $C_{1-10}$ alkyl.

6. The method of claim 1, wherein $R^3$ is $C_{1-10}$ alkyl and $R^4$ is hydrogen.

7. The method of claim 1, wherein $R^3$ is $C_{1-10}$ alkoxy-$C_{1-10}$ alkyl and $R^4$ is hydrogen.

8. The method of claim 1, wherein said inert aromatic solvent is a $C_{6-20}$ aromatic hydrocarbon solvent.

9. The method of claim 8, wherein said heating is conducted at a temperature of 75°–250° C.

10. The method of claim 9, wherein said heating is conducted at a temperature of 100°–200° C.

11. The method of claim 1, wherein $R^1$ is C(O)—$OR^5$, $R^3$ is $C_{1-10}$ alkyl or $C_{1-10}$ alkoxy-$C_{1-10}$ alkyl, $R^4$ is C(O)—$OR^5$ and X is I.

12. The method of claim 1, wherein $R^1$ is hydrogen, $R^3$ is $C_{1-10}$ alkoxy-$C_{1-10}$ alkyl, $R^4$ is hydrogen and X is I.

13. The method of claim 1, wherein $R^1$ is H, further comprising reacting said bipyrrole with a formylating agent to form a bipyrrole dialdehyde of the formula

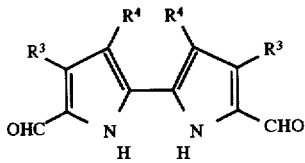

wherein $R^3$ is $C_{1-10}$ alkyl or $C_{1-10}$ alkoxy-$C_{1-10}$ alkyl and $R^4$ is hydrogen, $C_{1-10}$ alkyl or $C_{1-10}$ alkoxy-$C_{1-10}$ alkyl.

14. The method of claim 13, wherein said formylating agent is $POCl_3$ and dimethylformamide.

15. The method of claim 13, further comprising coupling two moles of said bipyrrole dialdehyde to form a porphycene having the formula

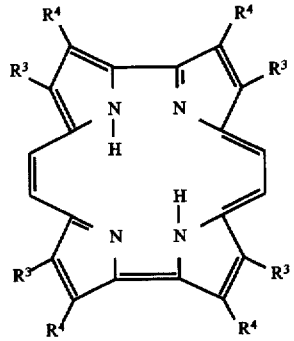

wherein $R^3$ and $R^4$ are, independently, hydrogen, $C_{1-10}$ alkyl or $C_{1-10}$ alkoxy-$C_{1-10}$ alkyl.

16. The method of claim 15, wherein said coupling is conducted in the presence of $Ti^{+2}$ or $Ti^{+3}$.

* * * * *